United States Patent
Martel et al.

(10) Patent No.: US 11,213,539 B2
(45) Date of Patent: Jan. 4, 2022

(54) USE OF IVERMECTIN AND BRIMONIDINE IN THE TREATMENT AND/OR PREVENTION OF MODERATE TO SEVERE ROSACEA

(71) Applicant: GALDERMA HOLDING SA, La Tour-de-Peilz (FR)

(72) Inventors: Philippe Martel, Biot (FR); Nabil Kerrouche, Le Rouret (FR); Fabien Audibert, Roquette-sur-Siagne (FR)

(73) Assignee: GALDERMA HOLDING SA, La Tour-de-Peilz (CH)

( * ) Notice: Subject to any disclaimer, the term of this patent is extended or adjusted under 35 U.S.C. 154(b) by 0 days.

(21) Appl. No.: 15/777,102

(22) PCT Filed: Nov. 17, 2016

(86) PCT No.: PCT/EP2016/078076
§ 371 (c)(1),
(2) Date: May 17, 2018

(87) PCT Pub. No.: WO2017/085226
PCT Pub. Date: May 26, 2017

(65) Prior Publication Data
US 2018/0344757 A1 Dec. 6, 2018

(30) Foreign Application Priority Data

Nov. 17, 2015 (EP) .................................... 15306822

(51) Int. Cl.
*A61K 31/7048* (2006.01)
*A61K 31/498* (2006.01)
*A61P 17/00* (2006.01)

(52) U.S. Cl.
CPC ........ *A61K 31/7048* (2013.01); *A61K 31/498* (2013.01); *A61P 17/00* (2018.01)

(58) Field of Classification Search
CPC .... A61K 31/7048; A61K 31/498; A61P 17/00
USPC ........................................................... 514/30
See application file for complete search history.

(56) References Cited

U.S. PATENT DOCUMENTS

| | | | | |
|---|---|---|---|---|
| 5,952,372 | A * | 9/1999 | McDaniel | A61K 31/35 514/453 |
| 8,669,233 | B2 * | 3/2014 | Jomard | A61K 9/0014 514/30 |
| 2004/0242588 | A1 | 12/2004 | Dejovin et al. | |
| 2006/0171974 | A1 * | 8/2006 | DeJovin | A61K 31/00 424/401 |
| 2011/0288096 | A1 | 11/2011 | Graeber et al. | |
| 2014/0249096 | A1 | 9/2014 | Jomard et al. | |
| 2015/0011489 | A1 | 1/2015 | Jacovella | |

OTHER PUBLICATIONS

Roso, "Management of Cutaneous Rosacea: Emphasis on New Medical Therapies", Expert Opinion on Phamacology, Sep. 4, 2014, vol. 15, No. 14, pp. 2029-2038, XP055330368, London, UK.
The International Search Report and Written Opinion dated Jan. 4, 2017, from corresponding Application No. PCT/EP2016/078076, filed Nov. 17, 2016.
Fowler, Jr. et al., "Efficacy and Safety of Once-Daily Topical Brimonidine Tartrate Gel 0.5% for the Treatment of Moderate to Severe Facial Erythema of Rosacea: Results of Two Randomized, Double-Blind, Vehicle-Controlled Pivotal Studies," Journal of Drugs in Dermotology, vol. 12, issue 6, pp. 650-656, 2013.

* cited by examiner

*Primary Examiner* — Shaojia A Jiang
*Assistant Examiner* — Michael C Henry
(74) *Attorney, Agent, or Firm* — Foley & Lardner LLP; Sunil Talapatra

(57) ABSTRACT

The present invention relates to a combination of ivermectin and brimonidine for use in the treatment and/or the prevention of moderate to severe rosacea, preferably by topical administration of a 1% ivermectin cream and 0.33% brimonidine gel.

7 Claims, 1 Drawing Sheet

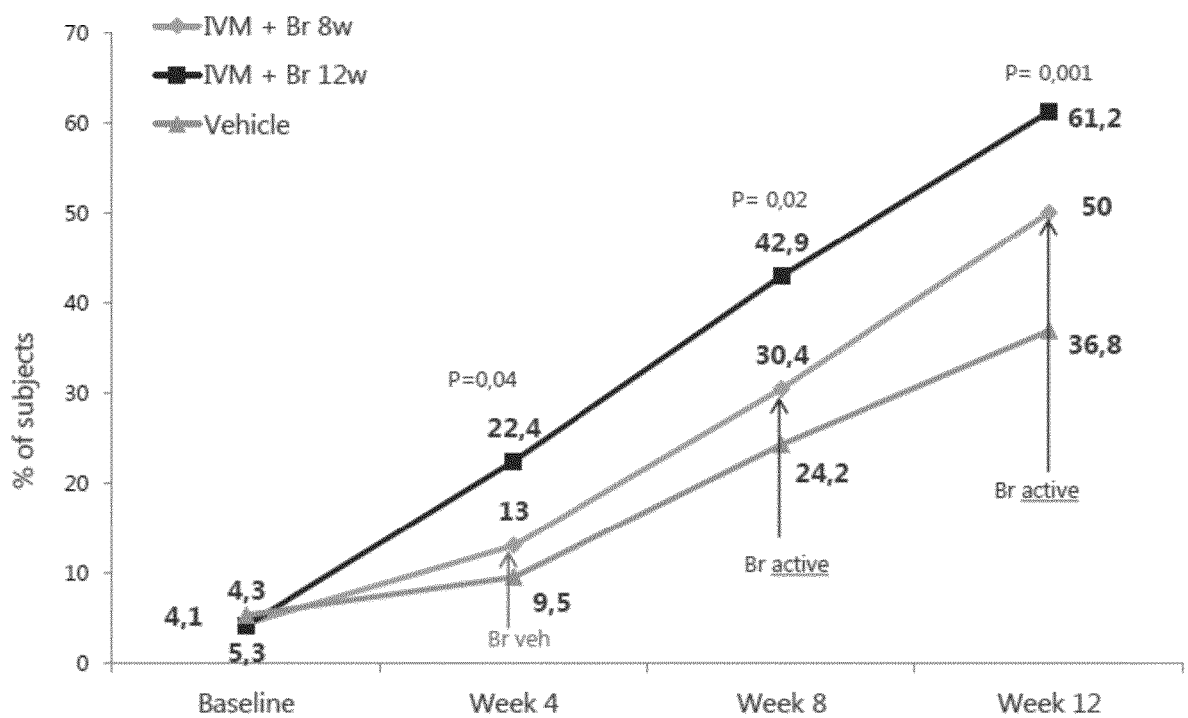

USE OF IVERMECTIN AND BRIMONIDINE IN THE TREATMENT AND/OR PREVENTION OF MODERATE TO SEVERE ROSACEA

CROSS-REFERENCE TO PRIOR APPLICATIONS

This application is a U.S. National Stage Application of PCT/EP2016/078076, filed Nov. 17, 2016 and designating the United States (published on May 26, 2017 as WO 2017/085226 A1), which claims priority under 35 U.S.C. § 119 of European Application No. 15306822.6, filed Nov. 17, 2015, each hereby expressly incorporated by reference in its entirety and each assigned to the assignee hereof.

BACKGROUND OF THE INVENTION

The invention relates to a combination of compounds for treating moderate to severe rosacea.

Rosacea is a common chronic and progressive inflammatory dermatosis related to vascular relaxation. It mainly affects the central part of the face and is characterized by a reddening of the face or hot flushes, facial erythema, papules, pustules, telangiectasia and sometimes ocular lesions called ocular rosacea. In serious cases, particularly in men, the soft tissue of the nose can swell and produce a bulbous swelling called rhinophyma.

Rosacea generally occurs between the ages of 25 and 70, and it is much more common in people with a fair complexion. It affects more particularly women, although this disease is generally more severe in men. Rosacea is chronic and persists for years with periods of exacerbation and remission.

The pathogenesis of rosacea is poorly understood. Many factors may be involved without necessarily inducing this disease. They are, for example, psychological factors, gastrointestinal disorders, environmental factors (exposure to the sun, temperature, humidity), emotional factors (stress), food-related factors (alcohol, spices), hormonal factors, vascular factors, or even an infection with *Helicobacter pilori*.

Papulopustular rosacea (PPR) is a chronic inflammatory disorder characterized by facial papules, pustules, and persistent erythema. In addition to neurovascular dysregulation, the facial skin of patients with rosacea is affected by augmented proinflammatory immune responses. The principal active cathelicidin peptide (LL-37) is highly concentrated in skin affected by rosacea and can contribute to acute inflammation. Moreover, PPR is characterized by the presence of inflammatory infiltrates that accompany flares, along with a heightened immune response involving neutrophilic infiltration and increased gene expression of IL-8.5 In addition to exogenous factors (including UV light, heat and alcohol), it may be triggered by *Demodex folliculorum* mites. Some studies of PPR observed higher mite densities compared to controls. Therefore, a multitude of factors can activate neurovascular and/or immune responses, and consequential inflammation leading to flares of rosacea.

LEGEND TO THE FIGURE

The FIGURE shows the efficacy of combining ivermectin and brimondine, according to the protocols described the Example (investigator's global assessment (IGA) score evaluated 3 hours after the application of the Brimonidine gel, at week 4, 8 and 12).

DETAILED DESCRIPTION OF THE INVENTION

The present invention relates to a combination of ivermectin and brimonidine for use in the treatment and/or the prevention of moderate to severe rosacea in a subject, preferably by topical administration of a 1% ivermectin cream and 0.33% brimonidine gel.

In a preferred embodiment of the present invention, the subject has moderate to severe papulopustular rosacea before the treatment.

In another preferred embodiment of the present invention, the subject has at least 10, preferably at least 12 and more preferably at least 15, inflammatory lesions of rosacea, before the treatment.

As used herein, the term "subject" means any animal, preferably a mammal, most preferably a human, to whom will be or has been administered compounds or topical formulations according to embodiments of the invention. Preferably, a subject is in need of, or has been the object of observation or experiment of, treatment or prevention of inflammatory lesions of rosacea or papulopustular rosacea.

As used herein, the term "inflammatory lesions of rosacea" include any type of skin lesions associated with the inflammatory phase of rosacea. Examples of "inflammatory lesions of rosacea" include various sizes of papules and pustules associated with rosacea. In a preferred embodiment of the present invention, the inflammatory lesions of rosacea comprise inflammatory lesions of papulopustular rosacea (PPR), more preferably inflammatory lesions of moderate to severe PPR.

In one embodiment, "treatment" or "treating" refers to an amelioration, prophylaxis, or reversal of a disease or disorder, or of at least one discernible symptom thereof. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

Success of treating inflammatory lesions of rosacea or PPR can be measured using methods known in the art, such as by the reduction of inflammatory lesion count from the baseline before treatment, by an improvement from the baseline in an investigator's global assessment (IGA) score, or by both the reduction of inflammatory lesion count and the IGA score.

The IGA score is determined by a trained medical professional evaluating the skin condition of a patient utilizing an investigative global assessment of the skin condition.

Typically, such global assessments assign a value to the degree of rosacea exhibited by the skin. In addition to the assessment made by the medical professional, the patient's input and observations of their skin condition and responses to various inquiries (e.g., stinging or burning sensations) also play a role in determining the IGA score that is assigned. For example, the IGA score for rosacea can range, for example, from 0 (clear) to 1 (almost clear) to 2 (mild) to 3 (moderate) to 4 (Severe), including values between these numeric gradings, such as 1.5, 2.6, 3.4 etc. (e.g., intervals of 0.1).

According to the invention brimonidine (optionally in form of its tartaric salt) and ivermectin are used in combination.

In the context of the present invention, brimonidine and ivermectin can be either present in the same composition, or, more advantageously, present separately from one another in separate compositions, forming for example a product in the form of a kit. In other words, these compounds are intended to be administered to a patient in the context of the same treatment, i.e. over a common period of treatment, either at the same time, optionally being included in one and the same composition, or at different moments. Furthermore, they can be administered by identical or different administration methods and/or be included in identical or different compositions.

In the case of a combination of the abovementioned compounds present separately in separate compositions, and in particular in the case of a product in the form of a kit, for use simultaneously, separately or with a time delay.

In a particular embodiment, ivermectin is topically applied every day in the evening and brimonidine is topically applied every day in the morning, during at least 12 weeks. In another particular embodiment, ivermectin is topically applied every day in the evening during at least 12 weeks and brimonidine is topically applied every day in the morning from the $3^{rd}$ to the $5^{th}$, preferably the fourth week, to the at least twelfth week.

In the compositions according to the invention, ivermectin is present at a concentration of between 0.001 and 10 percent by weight, relative to the total weight of the composition comprising it, preferably between 0.01 and 5 percent by weight, and in particular 0.75 percent, 1 percent, 1.5 percent or 2 percent. When a composition comprises several of these compounds, their total concentration is included in the abovementioned amounts.

In the compositions according to the invention, brimonidine is present at a concentration of between 0.01 and 20 percent by weight, relative to the total weight of the composition, preferably between 0.02 and 10 percent, particularly preferably between 0.05 and 5 percent by weight, relative to the total weight of the composition. Preferably the ivermectin is used at a concentration of 0.75 to 1.5%, whereas brimonidine is used at a concentration 0.05 to 1%.

The combination according to the invention and the compositions comprising the compounds of this combination are in particular intended for topical application to the skin, preferably in the form of dermatological compositions.

The term "dermatological composition" is intended to mean a pharmaceutical composition applied to the skin. The term "physiologically acceptable medium" is intended to mean a medium that is compatible with the skin, the mucous membranes and/or the skin appendages.

The compositions of the invention also comprise a pharmaceutically or cosmetically acceptable vehicle, i.e. a vehicle suitable for use in contact with human cells, without toxicity, irritation, undue allergic response and the like, and proportioned at a reasonable advantage/risk ratio.

The compositions of the invention may also comprise at least one other therapeutic agent capable of increasing the efficacy of the treatment.

The compositions of the invention may also comprise any additive normally used in the pharmaceutical or dermatological field.

Mention may in particular be made of sequestering agents, antioxidants, sunscreens, preservatives, for example DL-alpha-tocopherol, fillers, electrolytes, humectants, colorants, of customary inorganic or organic bases or acids, fragrances, essential oils, cosmetic active agents, moisturizers, vitamins, essential fatty acids, sphingolipids, artificial tanning compounds such as DHA, agents for soothing and protecting the skin, such as allantoin, propenetrating agents, gelling agents, or a mixture thereof. Of course, those skilled in the art will take care to select this or these optional additional compound(s), and/or the amount thereof, in such a way that the advantageous properties of the composition according to the invention are not, or not substantially, impaired. These additives may be present in the composition in a proportion of from 0 to 20 percent by weight, relative to the total weight of the composition.

The compositions of the present invention may be in any of the galenical forms normally used for topical administration, in particular in the form of solutions, lotions, gels, emulsions of liquid or semi-liquid consistency of the milk type, obtained by dispersion of a fatty phase in an aqueous phase (O/W) or vice versa (W/O), or suspensions or emulsions of soft, semi-liquid or solid consistency, of the cream or ointment type, or else microemulsions, microcapsules, microparticles or vesicular dispersions of ionic and/or non-ionic type.

Advantageously, the composition(s) comprise an ointment, a cream, a lotion or a gel. Preferably the ivermectin composition is in form of a cream, and the brimonidine composition is in form of a gel.

Example

1. Protocol:

Ivermectin (IVM) 1% cream and Brimonidine 0.33% gel are tested as an association. A vehicle controlled design allows for the generation of evidence of the association's impact on the inflammatory lesions and persistent erythema of rosacea along with safety and patient satisfaction after 12 weeks of therapy.

In order to explore different treatment introduction sequences within the association, the active arm has been split into two half arms: one with IVM 1% cream and Brimonidine 0.33% gel introduced jointly from baseline and one other with Brimonidine 0.33% gel introduced only after 4 weeks of vehicle.

Although not the study's primary objective, this design provides insight into the impact of these different regimens on patient satisfaction, in particular the influence of inflammatory lesion 'unmasking' by Brimonidine 0.33% gel in the early phase of treatment.

Objective(s):

The main objective of this study is to evaluate the efficacy of Ivermectin 1% cream (IVM) associated with Brimonidine 0.33% gel (Br) compared with the association of their respective vehicles in the treatment of moderate to severe rosacea. The Safety and Patient Reported Outcomes (PRO) are also evaluated.

Methodology:

This is a multi-center, randomized, double-blind, vehicle-controlled and parallel-group comparison study in subjects with moderate to severe rosacea characterized by persistent diffuse facial erythema and inflammatory lesions (papules and pustules). To allow assessment of the effect on Patient Reported Outcomes (satisfaction and QoL) of the introduction of Brimonidine 0.33% gel in the association, one half of the IVM/Br group subjects receive Brimonidine 0.33% gel from Baseline, and the other half, from week 4.

All eligible subjects are randomized in a 1:1:2 ratio, as follows:

Active Group (IVM/Br):

Half group (49 subjects) receives once-daily Br 0.33% gel in the morning and once-daily IVM 1% cream in the evening for 12 weeks.

Half group (46 subjects) receive once-daily Br vehicle gel in the morning for the first 4 weeks and once-daily Br 0.33% gel in the morning for the following 8 weeks and once-daily IVM 1% cream in the evening for 12 weeks.

Vehicle Group:

95 Subjects receive once-daily Br vehicle gel in the morning and once-daily IVM vehicle cream in the evening for 12 weeks.

Number of Subjects (Total), Number of Sites (Approximate Number of Subjects/Site), and Country(ies) Involved:

A total of 190 subjects (95 in active groups and 95 vehicle group) were enrolled at 26 sites in the United States of America, Canada and Germany.

Diagnosis and Main Inclusion Criteria:

Male or female subjects with moderate to severerosacea, age of 18 years or older, meeting specific inclusion/exclusion criteria.

Investigational Products:

Brimonidine 0.33% gel (Mirvaso® 0.5% gel in the US, Mirvaso® 3 mg/g gel in Europe, Onreltea® 3 mg/g in Canada).

Topical to the face, once-daily in the morning during 8 weeks for half of the group or during 12 weeks for the other half part of the group.

Ivermectin 1% cream (Soolantra® 1% Cream in the US, Soolantra® 10 mg/g in Europe and Rosiver® 10 mg/g in CANADA).

Topical to the face, once-daily in the evening 12 weeks

Comparator Products:

Brimonidine placebo gel. Topical to the face, once-daily in the morning during 4 weeks or during 12 weeks depending on the randomization scheme.

Ivermectin placebo cream: Topical to the face, once-daily in the evening 12 weeks.

Study Duration/Visits:

12 weeks, with up to 5 visits for subjects at Screening/Baseline, Week 4, Week 8, and Week 12.

Assessments:

Efficacy:

Severity of Rosacea Based on Investigator's Global Assessment (IGA) Evaluated by Investigators at Each Visit (Both Hour 0 and Hour 3)

The evaluator assesses the subject's rosacea at each visit prior to and 3 hours after the application of Br 0.33% gel or its vehicle, by performing a static ("snap-shot") evaluation using IGA score. No reference to previous visits is made by the evaluator, and IGA is evaluated before CEA, GSSIL assessments and inflammatory lesion count. A subject has an IGA of 3 (moderate) or 4 (severe) to be eligible for the study.

Severity on the Diffuse Persistent Facial Erythema of Rosacea Based on Clinician's Erythema Assessment (CEA) Evaluated by Investigators at Each Visit (Both Hour 0 and Hour 3)

The evaluator assesses the subject's diffuse persistent facial erythema of rosacea by performing a static ("snap shot") evaluation of erythema severity using CEA at each visit prior to and 3 hours after the application of Br 0.33% gel or its vehicle. A subject has a CEA of 3 (moderate) or 4 (severe) to be eligible for the study. The evaluator does not make any reference to previous assessments when evaluating the subject's erythema of rosacea and CEA is evaluated prior to GSSIL assessments and inflammatory lesion count.

Severity on the Inflammatory Lesions of Rosacea Based on Global Severity Score of Inflammatory Lesions (GSSIL) Evaluated by Investigators at Each Visit (Both Hour 0 and Hour 3)

The evaluator assesses the global severity of subject's inflammatory lesions of rosacea at each visit prior and 3 hours after the application of Br 0.33% gel or its vehicle, by performing a static ("snap-shot") evaluation using GSSIL score. No reference to previous visits is made by the evaluator, and GSSIL is evaluated prior to performing inflammatory lesion count.

Inflammatory Lesion Count by Investigators at Each Visit (Both Hour 0 and Hour 3)

The evaluator performs inflammatory lesion count on facial papules and pustules of rosacea at each visit prior to and 3 hours after the application of Br 0.33% gel or its vehicle. No reference to data of previous visits is made by the evaluator.

Inflammatory lesions are defined as follows:

Papule—A small, solid elevation less than one centimeter in diameter

Pustule—A small, circumscribed elevation of the skin, which contains yellow white exudates.

Papules and pustules are counted separately on each of the five facial regions (forehead, chin, nose, right cheek and left cheek). Nodules (defined as a circumscribed, elevated, solid lesion more than 1.0 cm in diameter with palpable depth) are not included in the count of inflammatory lesions, and subjects are not eligible if they have more than 2 nodules on the face at screening/baseline visit.

Severity of Stinging/Burning Evaluated by Subjects at Each Visit at Hour 0.

The evaluator records the severity of subject's facial stinging/burning sensation (a prickling pain sensation) during the last 24 h at each visit prior to the application of Br 0.33% gel or its vehicle after discussion with the subject.

Global Improvement in Rosacea Evaluated by Subjects at the Last Visit at Hour 3.

The subject evaluates his/her improvement in rosacea at week 12/early termination visit 3 hours after the application of Br 0.33% gel or its vehicle, compared with his/her rosacea condition before the study.

Safety

Adverse Events (AEs):

Adverse events are monitored throughout the course of the study. All AEs occurring after the subject signs the informed consent should be recorded on the AE form on the eCRF. All clinical medical events, whether observed by the investigator or reported by the subject and whether or not thought to be related to the study drug are considered AEs. Assessment of seriousness, severity and causality are based on specific definitions. If the subject discontinues due to an AE, both the AE Form and the Exit Form are completed. Subjects reporting a worsening of rosacea (worsening of any signs and symptoms of rosacea including but not limited to inflammatory lesions, persistent erythema and flushing) are evaluated in detail. This includes the onset, duration and outcomes of those events, as well as a complete history and potential triggers of the concerned signs and symptoms of rosacea. Pregnancy is not considered as an AE but is an important medical event, which is followed up.

Others

Dermatology Life Quality Index (DLQI) Questionnaire at Baseline, Week 4 and the Last Visit (Hour 0)

At Baseline, Week 4 and Week 12 early termination visit, prior to the application of Brimonidine 0.33% gel or its vehicle, subjects answer the 10-item DLQI questionnaire, a validated quality-of-life questionnaire specific to dermatological conditions.

EQ-5D Questionnaire at Baseline and Last Visit (Hour 0)

Subjects answer the quality of life questionnaire EQ-D5 at Baseline visit and the Week 12/early termination visit prior to the application of Brimonidine 0.33% gel or its vehicle. EQ-5D is a 5-level, 5-dimensional format standardized instrument for use as a measure of health outcome. Applicable to a wide range of health conditions and treatments, it provides a simple descriptive profile and a single index value for health status. EQ-5D was originally designed to complement other instruments but is now increasingly used as a 'stand-alone' measure. EQ-5D is designed for self-completion by respondents. It is cognitively simple, taking only a few minutes to complete.

The investigator or delegate then checks all questions of the questionnaire for completeness prior to the subject leaving the study visit.

Subject's Facial Appearance Satisfaction Questionnaire at Baseline, Week 4 and the Last Visit (Hour 0)

Subjects grade their satisfaction on their facial appearance at Baseline, Week 4 and Week 12/early termination visit prior to the application of Brimonidine 0.33% gel or its vehicle. Subjects have to indicate if their grading is related to papules/pustules, facial redness or both.

Subject Satisfaction Questionnaire at Last Visit (Hour 3)

At Week 12/early termination 3 hours after the application of Br 0.33% gel or its vehicle, subjects complete a questionnaire.

Photography at Each Visit (Both Hour 0 and Hour 3) at Selected Sites

Standardized photographs on the face (1 front view and 2 profile views) are taken at selected investigational sites at each study visit, prior to and 3 hours after the application of Br 0.33% gel or its vehicle. Pictures are used for illustrative purpose and are not subject to analysis.

Analyzed Variables:

Primary efficacy variable on ITT and PP population

IGA at Week 12 (Hour 3): % of subjects across scores

Secondary efficacy variables on ITT population

IGA at Each Intermediate Visit (Hour 0 and 3) and Week 12 (Hour 0): % of Subjects Across Scores CEA at each post-Baseline evaluation time: % of subjects across scores GSSIL at each post-Baseline evaluation time: % of subjects across scores Percent change from Baseline in Inflammatory Lesion count at each post-Baseline evaluation time Stinging/burning at each post-Baseline evaluation time: % of subjects across scores Global improvement in rosacea at the last visit (Hour 3): % of subjects across scores Safety variables on Safety population Incidence of Adverse Events Incidence of serious adverse events Other on ITT population (data observed)

DLQI questionnaire at Baseline, Week 4 and the last visit (Hour 0)

EQ-5D questionnaire at Baseline and last visit (Hour 0)

Subject Satisfaction Questionnaire at last visit (Hour 3)

Subject's facial appearance satisfaction questionnaire at Baseline, Week 4 and the last visit (Hour 0)

Principal Statistical Methods:

Centers considered too small may be combined to create analysis-center. The Intent-to-Treat (ITT) population consists of all enrolled and randomized subjects. The last observation carried forward (LOCF) method is used to impute missing values for IGA, GSSIL and inflammatory lesions. The definitions of analysis population and the pooling of centers are decided before the database lock.

The primary objective of this study is to demonstrate the superiority of the Active group (ie 2 half groups combined) compared to the Vehicle group, in terms of IGA at week 12, Hour 3. The primary efficacy endpoint is analyzed by using the Cochran-Mantel-Haenszel (CMH, FREQ procedure from SAS®) statistic, stratified by center (oranalysis-center) after ridit transformation with the row mean difference statistics, testing the hypothesis of equality. The p-value has to be inferior to 0.05 at week 12, on ITT/LOCF population. Per-protocol (PP) population analysis is also performed to assess the robustness of the results obtained on ITT/LOCF population.

The secondary efficacy variables, questionnaires is analyzed similarly as primary analyses on appropriate population.

All safety data are summarized per treatment group, based on the safety population. Adverse events are tabulated in frequency tables by System Organ Class (SOC) and Preferred Term (PT) based on MedDRA dictionary.

2. Results

The efficacy of the combination is shown on the FIGURE (IGA evaluated 3 hours after the application of the Brimonidine gel, at week 4, 8 and 12).

The below Table shows the results in term of safety.

| | IVM + Br veh 4 Weeks + Br 8 Weeks (N = 46) | | | IVM + Br 12 Weeks (N = 49) | | | IVM + Br Total (N = 95) | | | Vehicle (N = 95) | | |
|---|---|---|---|---|---|---|---|---|---|---|---|---|
| | Number of events | Subjects* N | % | Number of events | Subjects* N | % | Number of events | Subjects* N | % | Number of events | Subjects* N | % |
| Related AEs | 3 | 3 | 6.6 | 2 | 1 | 2.0 | 5 | 4 | 4.2 | 3 | 2 | 2.2 |
| Related Dermatologic Aes | 3 | 3 | 6.6 | 2 | 1 | 2.0 | 5 | 4 | 4.2 | 3 | 2 | 2.2 |
| Related worsening of Rosacea Aes | 1 | 1 | 2.2 | 0 | 0 | 0.0 | 1 | 1 | 1.0 | 3 | 2 | 2.2 |

| | IVM + Br veh 4 Weeks + Br 8 Weeks (N = 46) | | | IVM + Br 12 Weeks (N = 49) | | | IVM + Br Total (N = 95) | | | Vehicle (N = 95) | | |
|---|---|---|---|---|---|---|---|---|---|---|---|---|
| | Number of events | Subjects* N | % | Number of events | Subjects* N | % | Number of events | Subjects* N | % | Number of events | Subjects* N | % |
| Related severe Aes | 0 | 0 | 0.0 | 0 | 0 | 0.0 | 0 | 0 | 0.0 | 0 | 0 | 0.0 |
| Related serious Aes | 0 | 0 | 0.0 | 0 | 0 | 0.0 | 0 | 0 | 0.0 | 0 | 0 | 0.0 |
| Related AEs leading to discontinuation | 1 | 1 | 2.2 | 0 | 0 | 0.0 | 1 | 1 | 1.0 | 0 | 0 | 0.0 |

*Subjects with at least one event from screening to end of study. Numbers in columns cannot be added because a given subject may have reported more than one AE.
Related AEs = all related AEs are related to morning and evening treatments.

Interestingly, these results show that the related adverse effects when using the combination Ivermectin+Brimonidine are limited. This was not expected, as brimonidine, when used alone, was found to cause excessive related adverse effects in a number of patients, in particular a worsening of erythema that has been called a "rebound". Tanghetti et al, Journal of Drugs in Dermatology, 2015, 14(1):33-40 report such rebound in 10 to 20% of patients treated with brimonidine 0.33% gel.

The invention claimed is:

1. A method of treating rosacea in a subject in need thereof, comprising topically administering, daily for at least 12 weeks:
    (a) a composition comprising ivermectin in the form of a cream; and
    (b) a composition comprising brimonidine or salts thereof in the form of a gel,
    wherein:
    ivermectin is present in an amount of between 0.75 and 1.5 percent by weight, relative to the total weight of the composition comprising ivermectin;
    brimonidine or salts thereof are present in an amount of between 0.05 and 1 percent by weight, relative to the total weight of the composition comprising brimonidine; and
    the ivermectin and brimonidine are present separately within distinct compositions.

2. The method of claim 1, wherein ivermectin is present in an amount of 0.75, 1, or 1.5 percent by weight, relative to the total weight of the composition comprising ivermectin.

3. The method of claim 1, wherein brimonidine or salts thereof are present in an amount of 0.33 percent by weight, relative to the total weight of the composition comprising brimonidine.

4. The method of claim 1, wherein the composition comprising ivermectin is administered in the morning.

5. The method of claim 1, wherein the composition comprising brimonidine is administered in the evening.

6. The method of claim 1, wherein the composition comprising ivermectin is administered in the morning and the composition comprising brimonidine is administered in the evening.

7. The method of claim 1, wherein the ivermectin is present at a concentration 1 percent by weight, relative to the total weight of the composition comprising ivermectin.

* * * * *